United States Patent [19]
Ritter et al.

[11] Patent Number: 5,461,124
[45] Date of Patent: Oct. 24, 1995

[54] REACTIVE SYSTEMS AND/OR POLYMER COMPOSITION FOR TISSUE CONTACT WITH THE LIVING BODY

[75] Inventors: Wolfgang Ritter, Haan; Hans-Dieter Sitz, Rommerskirchen, both of Germany

[73] Assignee: Henkel Kommanditgesellschaft auf Aktien, Duesseldorf, Germany

[21] Appl. No.: 220,409

[22] Filed: Mar. 30, 1994

Related U.S. Application Data

[63] Continuation of Ser. No. 859,435, filed as PCT/EP90/01974, Nov. 19, 1990, abandoned.

[51] Int. Cl.$^6$ ............................. C08F 2/38; A61L 25/00; C28K 5/15
[52] U.S. Cl. ................. 526/84; 433/224; 523/111; 523/116; 523/118; 524/751; 524/752; 526/83; 526/204
[58] Field of Search ............................. 433/224; 523/113, 523/114, 115, 116, 118, 111; 524/751, 752; 526/83, 84, 204

[56] References Cited

U.S. PATENT DOCUMENTS

| | | | |
|---|---|---|---|
| 3,925,895 | 12/1975 | Kliment et al. | 433/224 |
| 4,585,726 | 4/1986 | Wallbillich et al. | 526/83 |
| 4,590,146 | 5/1986 | Wallbillich | 525/61 |

FOREIGN PATENT DOCUMENTS 0217153  9/1986  Japan.

OTHER PUBLICATIONS

Encyclopedia of Polymer Science and Engineering, vol. 10, pp. 1–15, John Wiley & Sons, 1987.
Introduction to Polymer Chemistry, John K. Stille, Chapter 4 pp. 34–40, John Wiley & Sons, 1962.
Characterization of Molecular Weight Distributions in High Polymers, Fred W. Billmeyer, Jr. Journal of Polymer Science, Part C No. 8, pp. 161–178, 1965.
Chemical Abstracts, vol. 89, No. 14, Oct. 2, 1978 (Columbus, Ohio, U.S.) Emanji, K. et al.: The Effects of a Tocopherol on Polymerization of Memethacrylate.
Chemical Abstracts, vol. 103, No. 18, Nov. 4, 1985 (Columbus, Ohio, U.S.) Emanji, K.: The Effects of α-tocopherol on Polymerization of Methylmethacrylate.

*Primary Examiner*—Peter A. Szekely
*Attorney, Agent, or Firm*—Wayne C. Jaeschke; John E. Drach; Henry E. Millson, Jr.

[57] ABSTRACT

Described is the use of physiologically compatible tocopherols and especially of vitamin E as an inhibitor against premature polymerization initiation in reactive systems capable of undergoing a free radical-initiated polymerization, which systems before and/or after the polymerization thereof are placed in tissue contact with the living human or animal body and, more specifically, are implanted into the living organism thereby. The reactive systems and the polymers formed therefrom may be degradation resistant. However, a special embodiment relates to compositions or molded bodies which are decomposed by the living organism, and especially so under time-controlled conditions. The invention further relates to surgical binder systems which are suitable for adhesion bonding endogenous body tissue and which have been based on an adhesive component capable of being activated by free radicals, said adhesive component being present in admixture with a free radical inhibitor and being characterized in that the inhibitor or at least the predominant portion of the inhibitor is vitamin E. It is preferred that the described compositions are free from physiologically unacceptable solvents or residual amounts of solvents left from the preparation process.

20 Claims, No Drawings

REACTIVE SYSTEMS AND/OR POLYMER COMPOSITION FOR TISSUE CONTACT WITH THE LIVING BODY

This application is a continuation of application Ser. No. 07/859,435 filed as PCT/EP90/01974, Nov. 19, 1990, now abandoned.

The invention relates to improvements in the field of reactive systems curable via free radical-involving mechanisms and/or polymer compositions obtained therefrom which are brought into tissue contact with the living body and which more particularly, when duly used, organism.

STATEMENT OF RELATED ART

In human medicine as well as in the field of veterinary medicine, polymer-based synthetic materials (plastics) and reactive systems curable upon the initiation of a reaction are increasingly gaining importance. Reference may be made to surgical and/or dental-medical adhesives, cements, filling compositions and the like, which after the application thereof and the implantation into the living organism will undergo curing and then will remain in contact with the living organism. Meanwhile, also concerned by the invention are pre-formed polymer materials comprised of, more particularly, pre-components reactive via free radicals, which polymer components, in the practical use thereof, can be purposefully shaped, but may also be introduced into the living organism just as a polymeric component of a mixture, for example of a reactive adhesive system. Nevertheless, to all these different embodiments there is likewise applicable that the pre-formed polymer is implanted into the living organism and here usually is exposed to an intensive action of the metabolism of the body.

In the discussed area of the use of synthetics and/or of reactive systems forming synthetic material in the living organism there are distinguished two following major classes: Non-degradable body-resistant synthetics incorporated in the living organism and designed to remain therein for either a limited or an unlimited period of time; on the other hand, there is the class of body-resorbable auxiliary materials of the kind mentioned, which under the action of the metabolism of the living organism are subject to a—preferably time-controlled—degradation and, as the case will be, ultimately will be completely resorbed. For example, duly degradable polymer components may be exemplified by surgical adhesives for adhesion-bonding endogenous hard tissue, and especially bones, wherein the binding function of the cured adhesive is designed to be replaced in the course the tissue regeneration—for example the bone growth. On the other hand, dental filling compositions and/or cements are demanded to consistently remain at the site of application. The same is applicable, for example, to cements and adhesives, respectively, for bonding implants—for example hip joint prostheses—in the human or animal organism.

Today there are numerous proposals for the use of synthetic materials (plastics) and curable reactive systems in and on the living body. A just exemplifying description thereof may be given by the selected field of use of the binder systems for adhesion-bonding endogenous hard-tissue, if so desired in combination with plastics and/or metal.

For solidly and permanently joining separated bone parts or to fix artificial implants in or on the bone or tooth material, there have so far been investigated poly (methacrylates), epoxide resin systems and polyurethane systems. Among these, predominantly the poly(methacrylates) have become accepted in practice. They are mainly suitable for the implantation of joint prostheses, cement-metal osteosynthesis, vertebral column fusions and defect covers on the skull cap and/or implants of supporting material in face surgery. The cements, adhesives and like as used here conventionally are not resorbable by the organism.

DESCRIPTION OF THE INVENTION

In addition to the above-mentioned applications, there is a desire to offer additional field of use for bone adhesives and/or bone cements, for example in connection with an anatomic reposition, fixation and retention of bone fragments in cases of comminuted or articular fractures. Here, a reversible reposition, fixation and retention of bone fragments by means of resorbable adhesive systems appears to be particularly desirable. Then, the bone adhesive or cement is intended to be resorbed synchronously with the bone regeneration. Of further importance is the reversible stabilization of fractures by means of plates or splints which are secured by means of resorbable adhesives. In these cases, if splints or plates made of metal or plastics are used, it is not necessary to provide drill holes in the bone and to use screws and bolts. Furthermore, upon the use of resorbable supporting materials, e.g. made of polylactic acid or polyglycolic acid, a second surgery would no longer be required.

The curable adhesives so far employed in practice, especially those based on methacrylate systems, consist of the following components:

One or more monomers polymerizable via free radicals, said monomers being present in admixture with inhibitors designed to prevent a premature free radical-initiation of the reaction.

A free radical-initiator system for initiating the polymerization, said system with respect to kind and amount thereof being sufficient to overcome the inhibiting action of the above-mentioned stabilizers.

Polymers for improving the cohesion and for adjusting the vicosity;

optionally active fillers for improving the mechanical properties.

As the polymerizable monomers, numerous further systems have been investigated in addition methyl methacrylate in combination with methacrylic acid; some of these systems have gained practical importance; hereto cf. J. M. Antonucci, Polymer Science and Technology 14, 357 (1981). Also on the side of the curing agents, today a wide selection of accelerators is available— cf., for example, G. M. Brauer, Org. Coat. Plast. Chem. 42, 321 (1980) as well as J. W. Prane, Org. Coat. Plast. Chem. 40, 338 (1979).

Applicants, in a plurality of proposals, suggested organoboron compounds for the polymerization initiation of the systems involved here; hereto cf., for example, the German Patent Applications DE 32 29 635 A1 and DE 32 01 780 A1. It is the object of the invention, in a controlled manner to improve the physiological compatibility in tissue contact with the living body of such systems that are reactive via free radicals or have completed their reaction by free radical-initiated polymerization and/or curing. The invention pertains to both the area of the non-resorbable auxiliary materials and the area of the body-resorbable materials.

Thus, in a first embodiment the invention starts from considering the following facts:

It is basic chemical knowledge that in the production, transportation and/or storage of systems that are reactive via free radicals it is necessary to concomitantly use free radical-inibitors for definitely excluding that the system will undergo any premature reaction. Here, in practice there is known the addition of numerous compounds and/or systems, including, for example, hydrides such as lithiumaluminum hydride, calcium hydride or sodium borohydride. Further known examples serving this purpose are phenols, phenol derivatives, hydroquinone and hydroquinone derivatives or, especially, phenothiazine. As typical examples there may be mentioned cumene, hydroquinone, 2,6-di-tert.-butyl-p-cresol, 2,6-di-tert.-butyl-4-methoxyphenol, bis(2-hydroxy-3-tert.-butyl-5-methylphenyl)methane, bis(3,5-di-tert.-butyl-4-hydroxyphenyl)methane, bis(2-hydroxy-3-tert.-butyl-5-methylphenyl)sulfide, bis( 3-tert.-butyl-4-hydroxy-5-methylphenyl)sulfide, or also amines such as diphenylamine, N,N'-diphenyl-p-phenylene diamine, 2-phenylbenzimidazole, aniline, dinitrobenzene, 2-nitro-α-naphthol, tetraphenylethylene and triphenylmethane.

Such free radical-inhibitors, most commonly are required not only for the safe storage of the system to the date of the application thereof; it is rather necessary to employ such initiators already in the preparation of the free radical-reactive compounds—for example the (meth)acrylic acid esters—. Thus, one may distinguish between the so-called "preparation inhibitors" and the "application inhibitors", where both of these types of inhibitors may be same or different with respect to the kind and amount thereof. In the former case, the application inhibitor in general is identical with the preparation inhibitor already used in the preparation. However, it rather often occurs that the drastic or otherwise difficult conditions of the preparation of the free radical-reactive components demand the use of comparably strongly active preparation inhibitors, the concomitant use of which is undesirable in the field here concerned of use on or in the living body.

In appreciation of these facts, the invention provides the concept of using a selected inhibitor having an optimal compatibility with the body in the reactive or reacted plastics material getting into contact with the living body. The inhibitor selected according to the invention is represented by physiologically compatible tocopherol compounds, and especially vitamin E.

Thus, the invention, in this first embodiment, relates to the use of vitamin E as an inhibitor against premature polymerization initiation in reactive systems capable of undergoing a free radical-initiated polymerization, which systems before and/or after the polymerization thereof are placed in tissue contact with the living body and, more specifically, are implanted into the living organism thereby.

In a preferred embodiment, vitamin E is employed as the at least predominant constituent of the application inhibitor system of surgical and/or dental-medical reactive adhesives and/or cements or corresponding fillers. This preferred embodiment of the invention further comprises the use of vitamin E as the at least predominant constituent of the application inhibitor system in polymer compositions that have been prepared before the incorporation thereof in living tissue.

The physiological importance of vitamin E in metabolism and, more specifically, its function of protecting from an undesirable free radical-initiated attack to the living cell or cell constituents have been generally recognized today. Accordingly, vitamin E is widely used, e.g. in the form of capsules, in high doses in externally applicable skin-protective agents such as suntan creams and the like and as an additive to foodstuff. The compatibility of vitamin E even in high doses in its interaction with the living organism has been ascertained. Thus, for the technical purpose of inhibiting reactive systems against a premature initiation of the reaction, the invention provides the use of a substance which—in contrast to numerous other known inhibitors for this field of use—possesses optimal physiological compatibility. But also the use of vitamin E in pre-formed polymer compounds involves a comparable advantage. Also the polymer compositions pre-formed outside of the body, once implanted into the human body, will be subject to an intensive material exchange with the living organism. Thus, especially upon a long-term action, at least a partial leaching of the initially employed inhibitor system and, hence, a correspondingly resulting stress on the living organism, will have to be expected. This process which in fact cannot be stopped is virtually irrelevant in the light of the teaching according to the invention.

According to invention it may be preferred to employ vitamin E as the only application inhibitor, so that the use thereof in amounts of from about 200 to 10,000 ppm may be contemplated. Usually preferred are quantities of vitamin E ranging from about 300 to 4,000 ppm—always based on the weight of the free radical-reactive mixture before or after it has been cured. The reactive composition of the kind concerned here may be mono-component or multi-component medical and/or dental-medical adhesives, cements or fillers based on conventional monofunctional and/or polyfunctional olefinically unsaturated compounds. In this context, particular importance is attached to acrylic acid and/or methacrylic acid or the derivatives thereof, especially with monofunctional and/or polyfunctional alcohols, for the sake of simplicity designated as (meth)acrylates hereinbelow.

In an important embodiment of the invention, the vitamin E is provided not only as the application inhibitor. Here it is preferred to also employ the vitamin E already as the preparation inhibitor in the synthesis of the reactive and/or already reacted components of the compositions designed to get into contact with the living organism. Here, an undesirable transfer of inhibitor or inhibitor portions from the preparation of the reactive components into the system ultimately used and, hence, an implantation of undesired inhibitor constituent into the living organism are reliably prevented. Nevertheless, this variant of the invention will gain its particular importance only if the purification of the free radical-reactive material by removing its preparation inhibitors will give rise to trouble. The broad scope of the auxiliary materials and working materials concerned here also includes embodiments wherein such a removal of the preparation inhibitor by means of conventional methods, for example by distillative purification, is possible. In all of these cases there is largely freedom with respect to choosing the preparation inhibitor for producing the reactive system. For example, highly reactive inhibitor systems such as phenothiazin, substituted hydroquinone compounds and the like may be selected. After the synthesis of, for example, a monomeric (meth)acrylate, the reactive compound may be separated by distillation from the low-volatile inhibitor. The reactive material thus purified is then stabilized within the meaning of the invention by means of vitamin E and is put into use in this form.

On the other hand, it may be just in the field of adhesives that the distillative purification of the reactive components and, thus, separating them from an unsuitable preparation inhibitor is difficult to achieve or even impossible. Adhesive systems which, for example, at least in part contain polyfunctional high-boiling esters of (meth)acrylic acid with polyfunctional alcohols will already have to be modelled by selecting the preparation inhibitor in consideration of the teaching according to the invention. Here, a distillative separation of the preparation inhibitor most commonly will not be applicable. Then, the use of vitamin E as inhibiting additive already in the step of producing the reactive low-volatile compounds may already offer itself.

Nevertheless, in a further embodiment even in components of the kind last-described, an inhibitor exchange will be possible and is provided such as that described, more particularly, in Applicants' U.S. Pat. No. 5,278,336, "Process for exchanging inhibitor(s) in olefinically unsaturated systems which are reactive via free radicals". According to the teaching of this parallel protective right there are used, as the preparation inhibitors, appropriate compounds of the phenol type having hydroxyl groups capable of undergoing salt formation, which compounds—after the preparation of the reactive compounds—will be caused to react with, and thereby to be bound to, solid basic components, and especially solid oxides and/or hydroxides of the alkaline earth metals, and will be removed from the reaction mixture. As to details, reference is made to the above-mentioned parallel application. Then, according to the invention, the removed preparation inhibitor or the respective portion thereof is replaced by vitamin E as the application inhibitor.

In a preferred further embodiment, vitamin E is used as an inhibitor in materials of the kind described which are reactive via free radicals and/or have already completed the reaction and which are free from physiologically unacceptable solvents or residual amounts of solvent left from the preparation. Also here, particular importance may be attached to those components which by themselves cannot be purified as a volatile phase in a distillative procedure. Again this is especially applicable to polyfunctional low-volatile constituents of the reactive mixture which are obtained, for example, by the reaction of (meth)acrylic acid with polyfunctional hydroxyl compounds. Systems of this last-mentioned type even during the synthesis thereof are highly susceptible to gelling. According to prior art, the danger of a premature initial or complete reaction is reduced by employing solvents in the preparation of the respective polyfunctional low-volatile components, in order to reduce the danger of a premature gelling by the dilution effect. Then, the comparably readily volatile solvents are withdrawn by distillation, in which step it is often attempted also to remove the last solvent residues by means of an extended treatment in high vacuum. It has been found that quite generally the really complete removal of the solvents is difficult, so that this constitutes another source of an unnecessary stress of the living organism in the course of the implantation of a reactive system or a molded part made therefrom. In the described preferred embodiment of the invention, such a stress is also intended to be reliably eliminated. Accordingly, any concomitant use of, more specifically, physiologically unacceptable solvents is a priori prevented in the adhesives, fillers and/or the corresponding mixing components.

It will be readily understood that the proposals according to the invention provide important improvements for the particularly sensitive field of the synthetic materials (plastics) or plastics-forming reactive systems in the interactions thereof with the living organism. This is applicable to degradation-resistant compositions and/or molded articles of the kind mentioned as well as, more particularly, to materials that are degraded by the living organism and, thereupon, are subject to a time-controlled resorption.

The invention, in a further embodiment, finally relates to surgical binder systems which are suitable for adhesion-bonding endogenous tissue and are based on a free radical-activatable adhesive component present in admixture with a free radical-inhibitor, this teaching according to the invention being characterized in that the inhibitor or at least the predominant proportion of the inhibitor is vitamin E. More specifically, said binder is also free from physiologically unacceptable solvents or solvent residues entrained from the preparation.

Here especially suitable are conventional (meth)acrylate two-component adhesives which, however, now are characterized by their content of vitamin E as inhibitor. Two-component adhesives of this kind usually consist of methyl methacrylate, acrylic acid, polymethyl methacrylate (= monomer resin) and an initiator system. These adhesives are used in medicine as bone cement for anchoring implants (J. Lehmann, Deutsche Apothekerzeitung, 128th Year, No. 29, Pages 119 et seq.).

According to the invention, the monomers employed have been freed from preparation inhibitors as used on a commercial large scale, e.g. by distillation, and instead have been inhibited with vitamin E. In the preferred embodiment, also the polymethyl methacrylate employed as a component of the mixture is prepared from a monomer containing vitamin E as inhibitor. Products thus prepared are less toxic, while the adhesion-technological properties thereof remain unchanged. Adhesive resins of this kind may be polymerized by way of a conventional redox catalysis—for example by peroxide/amine systems—as well as by the action of UV light in the presence of UV initiators, but also by the use of alkylboron compounds such as those described, for example, in Applicants' German Laid-Open Patent Applications (all DE-A1) 30 41 843, 30 41 904, 31 43 945 and 32 01 780.

Especially contemplated within the scope of the invention, in this embodiment, are also polyfunctional (meth-)acrylates which preferably have been prepared in the absence of solvents like those described—including the preparation thereof—in the older Patent Applications P 38 43 854.2 (D 8492), P 38 43 938.7 (D 8493), P 38 43 930.1 (D 8494), P 38 43 843.7 (D 8483). More specifically, in the Patent Application P 38 43 930.1 (D 8494) there has at the same time been described already the use of vitamin E as a preparation inhibitor. Here, the polymer compositions formed by completion of the reaction usually are not resorbable by the body.

However, adhesive components particularly suitable for the use within the scope of the present invention are oligomer components such as those described in Applicants' previously published German Laid-Open Patent Applications (both DE-A1) 32 04 504 and 32 29 635. These systems may find use as surgical binders or adhesives for adhesion-bonding endogenous tissue and/or for the in situ formation of molded plastics articles in the course of surgical work in human and veterinary medicine. One particular inherent property of these materials is that they are resorbable by endogenous degradation reactions, where, if so desired, the time required for the resorption process can also be affected. Binder systems of this kind are distinguished in that they at least partially contain, as the resorbable (meth)acrylate component, (meth)acrylic acid esters that are liquid to solid at room temperature and contain (meth)acrylate moieties on polyesteroligomer chains formed from hydroxycarboxylic acids. These components which are reactive via free radicals may comprise one, or preferably also several, (meth)acrylic acid group(s) on the polyesteroligomer segment. Particularly suitable may be reactive components having from 2 to 4 (meth)acrylate moieties on the oligomer segments and which optionally are used in admixture with only olefinically mono-unsaturated (meth)acrylate components.

Adhesive systems based on such reactive components are distinguished by a plurality of desirable properties. They have a low volatility due to the low vapor pressure thereof. In spite of their comparably high molecular weights there is a possibility of forming them at room temperature as liquids or at least as viscous spreadable pastes. They exhibit good miscibility with the further components conventionally used in the binder systems here concerned. They are capable of providing resilient adhesion bonds having high strength. More particularly, these selected reactive monomers result in cured synthetics which can be resorbed by the liquid organism. Thus, the use thereof in the course of surgical work leads to the reversible formation of adhesion bonds, supporting and holding members and the like which, for example, with bone fractures display an action for a limited time, while they are ultimately decomposed by resorption.

In those types of compounds having 2 (meth)acrylate moieties in the molecule, which are particularly important for practical use, these functional groups are preferably located in terminal positions of the oligomer so that both of the terminal moieties of the oligomer segment have been substituted with a (meth)acrylate group each (α,ω-positions).

The oligomer segments comprise the structural feature

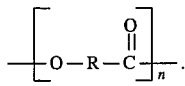

They are obtainable by oligomerization of suitable hydroxycarboxylic acids or hydroxycarboxylic acid mixtures having the general formula

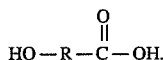

In a preferred embodiment of the invention, the moieties —R— and the value of n have been selected so that the number average molecular weight of the polyester oligomer unit is within the range of from about 200 to 600. Especially preferred values for the number average molecular weight are within the range of from about 300 to 500.

In a preferred embodiment, the polyester oligomer segment is formed from monohydroxy-monocarboxylic acids comprising not more than about 20 carbon atoms in a molecule thereof, and preferably not more than 10 carbon atoms. In this context, lower hydroxycarboxylic acids having from 2 to 6 carbon atoms can be especially important. Hydroxycarboxylic acids that are particularly suitable to form this centerpiece of the (meth)acrylate compounds are glycolic acid, the isomeric lactic acids, the optionally isomeric α- or β-hydroxypropionic acids, the optionally isomeric α-, β- or γ-hydroxybutyric acids, o-hydroxybenzoic acid (salicylic acid), m-hydroxybenzoic acid and/or p-hydroxybenzoic acid (anisic acid). Either definite isomers of said acids or any optional mixture thereof may be employed.

The polyester oligomers expediently have been prepared with the concomitant use of monofunctional and/or preferably polyfunctional reactants. The co-reactants will control the average molecular weight in the polyester oligomer and, thus, adjust the desired viscosity range. On the other hand, the selection of the functional groups of the concomitantly used co-reactants makes it possible, uniformly to have formed terminal hydroxyl groups or terminal carboxyl groups. Finally, a concomitant use of pre-selected co-reactants allows to successfully eliminate a reactive terminal group of the polyester oligomer so that in this type of compounds only one reactive function will be available for the subsequent attachment of the (meth)acrylate residues. Finally, by employing of a suitably selected admixture of monofunctional and polyfunctional co-reactants it will be possible to realize pre-determined mixing ratios of mono-(meth)acrylate compounds and polyfunctional (meth)acrylate compounds.

Suitable monofunctional co-reactants, more particularly, include monoalcohols and/or monocarboxylic acids. Polyfunctional co-reactants in the preparation of the polyester oligomers are polyfunctional alcohols, and especially di- to tetrahydric alcohols, or the corresponding polycarboxylic acids and the functional reactive derivatives thereof. Co-reactants with functional hydroxyl groups are preferred. Here, particular importance my be attached to lower polyfunctional alcohols such as ethylene glycol, propandiol, especially 1,2-propane diol, glycerol and the like.

In all cases there are formed modified polyester oligomers which in a per se known manner can be readily reacted to form reactive (meth)acrylate compounds. If terminal hydroxy groups are present in the polyester oligomer, then the (meth)acrylic acid group(s) will be introduced by esterification or transesterification with acrylic acid or acrylic acid esters and/or especially the corresponding methacrylic acid compounds.

In a preferred embodiment of the invention, (meth)acrylate compounds or appropriate mixtures thereof are employed, which are fluid or at least still pastous and spreadable at room temperature, so that they can be utilized in the binders as the major component or even as the only polymerizable component of the adhesive. It may be preferred that the (meth)acrylate compounds have a viscosity at room temperature within the range of from about 500 to 70,000 mPa.s, and preferably within the range of from about 3,000 to 50,000 mPa.s. However, solid (meth)acrylate compounds of the indicated type will be readily dissolved in liquid polymerizable components, for example in methyl methacrylate, so that also solid compounds of the reported constitution can be easily processed in admixture with liquid conventional monomer components to form the process-technologically desired fluid or spreadable adhesive components.

The solvent-free preparation of (meth)acrylic esters of polyhydric alcohols with the concomitant use of tocopherols, and especially of vitamin E, and the purification of the crude reaction products obtained thereby has been described in Applicants' older Patent Application Ser. No. 07/859,428 filed Jul. 27, 1992, in favor of Ser. No. 08/278, 680 filed Jul. 21, 1989 pending "Process for the improved preparation of (meth)acrylic acid esters of polyhydric alcohols"). According to what has been disclosed in said older protective right, reaction mixtures are employed which are liquid at room temperature, at least largely free from solvents and/or azeotropic entrainers while using vitamin E as the preparation inhibitor. The condensation water formed in the esterification reaction is withdrawn from the gaseous phase of the reaction space. It is preferred that reaction space is flushed with a gas stream containing free oxygen, to which end air or a gas mixture enriched with $O_2$, and especially the corresponding nitrogen/air mixtures, may be employed. The esterification is preferred to be carried out at bottoms temperatures of at least about 90° C., and preferably of at least about 100° C., and especially within a range of up to about 150° C., at least stage-wise operating under reduced pressure, and optionally under a stepwise increasingly reduced pressure. The vitamin E used as the preparation inhibitor in this reaction is conveniently employed in amounts of from 200 to 10,000 ppm, and preferably in amounts falling within the range of from 300 to 4,000 ppm—each based on the weight of the reaction mixture. Under the conditions as mentioned of the absence of a solvent and/or entrainer, the reaction may be conducted to a conversion of at least 90% of the theory. In the course thereof—with the preferred operation within the temperature range of from 100° C. to 140° C.—periods of reaction of 10 hours, and especially of 8 hours are not or not essentially exceeded. The crude reaction product may be subjected to a dry neutralization— preferably with oxides and/or hydroxides of the alkali metals, alkaline earth metals and/or of aluminum. Such working conditions are suitable also for the preparation of the last mentioned body-resorbable polyfunctional (meth)acrylates.

Numerous initiator systems are suitable for reactive systems of the last-described kind. These include, more particularly, redox systems such as the known system of dibenzoyl peroxide/dimethyltoluidine. Likewise, alkylboron compounds above all are suitable to initiate the polymerization, such alkylboron compounds having been described in greater detail in Applicants' previously published protective rights as cited. In this context, particular reference is once more made to the DE-OS (A1) 32 29 635 as well as to the parallel Patent Application Ser. No. 07/859,428, abn. in favor of Ser. No. 08/278,680 Jul. 21, 1994 pending "New initiator systems for initiating the polymerization of ethylenically unsaturated compounds and use thereof").

In Applicants' last-mentioned parallel application there have been described initiator systems based on oxygen-reactive organoboron compounds for initiating the polymerization of ethylenically unsaturated compounds, which systems are characterized in that they contain, as carriers, oligoesters of lower hydroxycarboxylic acids. Thus, here also the carriers of the initiator system are body-resorbable substances. More particularly, suitable carriers are oligoesters of hydroxycarboxylic acids having from 2 to 10 carbon atoms, and preferably having from 2 to 5 carbon atoms, among which the oligoesters of glycolic acid and/or lactic acid are of particular importance. Especially suitable oligoesters are low-viscosity reaction products which preferably have viscosities within the range of up to 40,000 mPa.s, and especially of up to a maximum of about 25,000 mPa.s—each determined at room temperature. The respective low-viscosity reaction products are prepared with the concomitant use of alcohols and/or carboxylic acids, preferably with the use of polyfunctional alcohols; among these, the reaction products from ethylene glycol and/or glycerol with glycolic acid and/or lactic acid may be of particular importance.

Finally, also the use of UV light in combination with UV-initiators is a suitable means for initiating the reaction.

Thus, the teaching of the invention covers a multitude of reactive systems which may be optimally tailored to meet the requirements set by the intended area of use.

The reactive components forming may be resistant to degradation or may be degradable by the body. The same is applicable to pre-formed polymers as possibly included in the use. Also the initiator systems providing the concomitant use of oligomeric or polymeric carriers optionally can be formed to be either degradation-resistant or body-resorbable and may be adapted to be combined with the total system.

There is consistently applicable to all of the embodiments of the invention that vitamin E is of an outstanding importance at least as an application inhibitor and that in the preferred embodiments the compositions are free from solvents and even residual amounts of solvents.

The following Examples describe characteristic embodiments of the invention for conventional non-degradable reactive adhesives as well as for body-resorbable adhesives of the kind mentioned above.

EXAMPLES

EXAMPLE 1

1. Adhesive resin
a) Distillation of the monomers methacrylic acid and methyl methacrylate Distillation of the methacrylic acid (for removing hydroquinone monomethylether) and direct new inhibition using vitamin E In a vacuum distillation apparatus, 15 moles (= 1,291.35 g) of methacrylic acid (b.p. 163° C.) were admixed with 3.87 g (= 3,000 ppm) of phenothiazine (as stabilizer); the methacrylic acid was distilled off under a strong stream of air in a water-jet vacuum. 100 ppm of vitamin E (Covitol F-1000-2, 67%, Henkel KGaA= 139 mg/l) are placed in the receiver, and the methacrylic acid is distilled with stirring. The distillation is stopped, once 932 g of the methacrylic acid have been collected after distillation.

Distillation of methyl methacrylate (for removing hydroquinone) and direct new inhibition using vitamin E The distillation is carried out in the same manner as the distillation of methacrylic acid.

b) Preparation of the adhesive resin
General procedure

In a beaker, 40 g of polymethacrylic acid methyl ester (PMMA) were dissolved with stirring in 45 g of methacrylic acid methyl ester (MMA) and 5 g of methacrylic acid (MAS) which had been distilled as described under 1. a).

c) Tests of adhesion bonding
using an alkylboron hardener

To 10 g of this mixture there were added with further intensive stirring 3% by weight of the alkylboron initiator as described in 2 a). The pot life of the mixture was 4 minutes. Using these adhesives there were bonded within the pot-life sand-blasted and degreased iron sheets, and the strengths were measured in the tensile shear test according to DIN 53 281/3 after 24 hours. The results are compiled in Table 1.
using a peroxide/amine hardener for the adhesive resin To 10 g of the monomer resin according to 1 b) there were added with further intensive stirring first 1% by weight of N,N-dimethyltoluidine and then 2% by weight of dibenzoyl peroxide (as Lucidol paste DBP 50%), and the product was intensively mixed. The pot life of the mixture was 1.5 minutes. The resulting tensile shear strengths are also listed in Table 1.

2. Preparation of the alkyl boron hardener
Preparation of the oligomers
General procedure for preparing the reaction products of lactide with glycerol The lactide {L(−)-lactide N of the company Boehringer, Ingelheim} and glycerol were heated to 105° C. under nitrogen and with stirring in a conventional laboratory apparatus within one hour while catalyzed with 0.5% of phosphoric acid—relative to lactide. The mixture was then allowed to react at 195° C. for 6 hours and dispensed while hot. The following products were prepared:

| a) Lactic acid: | glycerol = 3:1 |
|---|---|
| Charged: | 432 g of lactide = 3 moles |

|  |  | 184 g of glycerol = 2 moles |
|---|---|---|
|  | Yield | 610 g = 99% |
| b) | Lactic acid: | glycerol = 2:1 |
|  | Charged: | 1 008 g of lactide = 7 moles |
|  |  | 644 g of glycerol = 7 moles |
|  | Yield | 1 621 g = 98.2% |

The composition of the resulting products and the properties thereof are set forth in Table 2.

Preparation of the Boronoligomer adduct

General procedure for preparing the boronalkyl hardener from lactic acid oligomers according to 2. and 9-BBN A three-neck flask equipped with stirrer and thermometer was charged with 100 g of the oligomer according to 2.a) or 2.b). After heating to about 50° C., the flask was evacuated with a rotary slide-valve vacuum pump to 1 mbar two times for ten minutes each, and each time with nitrogen re-filled to atmospheric pressure.

Subsequently thereto, the amounts set forth in Table 3 of 9-bora[3.3.1]nonane (9-BBN) were added in a nitrogen stream. For improving the process control, 100 ml of THF (stored over $FeCl_2$) were distilled into the reaction mixture through a column head. The reaction mixture was maintained under a nitrogen stream at about 60° C. to 65° C. for 1.5 hours. Then the THF was distilled off at about 60° C. with the use of water-jet pump vacuum, and the residual amounts of THF were withdrawn at 1 mbar. The reaction product was transferred under a nitrogen stream into a storage vessel and stored in the closed vessel under $N_2$.

The preparation of the hardeners and the properties thereof are compiled in Table 3.

TABLE 1

Survey of the measured values of the tensile strength [in N/mm²]

| Monomer adhesive resin g | Hardener component Type | Amount added % by weight | Pot Life minutes | Strength to Fe sheets after 24 hours at room temperature N/mm² | Boron content in the adhesive % by weight |
|---|---|---|---|---|---|
| 10 | Alkylboron according to 2 a) | 3 | 4 | 27 | 0.11 |
| 10 | Dimethyltoluidine/dibenzoyl peroxide | 1 | 1.5 | 25.6 |  |

TABLE 2

Oligohydroxycarboxylic acids from glycerol and lactide

| Example | Glycerol | Lactide | Consistency at room temperature | Viscosity Epprecht-Viscosimeter/MK 4 at room temp. mPa · s |
|---|---|---|---|---|
| a | 1 | 1.5 | clear, slightly viscous | 18,000 |
| b | 1 | 1 | slightly yellow, slightly viscous | 16,500 |

TABLE 3

Preparation of the initiator components a 1, a 2, b

| No. | Oligomers: lactic Acid: glycerol | Amount of 9-BBN employed: grams per 100 g of substance | Product properties | Amount of boron % by weight |
|---|---|---|---|---|
| a 1 | 3:1 | 41 | homogeneous colorless, viscous | 3.64 |
| a 2 | 3:1 | 20 | homogeneous colorless, viscous | 1.78 |
| b | 2:1 | 41 | homogenous, bright yellow, colorless | 3.64 |

EXAMPLE 2

A body-resorbable and vitamin E-stabilized adhesive component based on oligoglycolic acid/bis-methacrylate is prepared in the following process steps:

First, an oligomer having terminal hydroxy groups is prepared from glycolic acid and ethylene glycol in a molar ratio of 4:1. Then, commercially available methacrylic acid with the addition of phenothiazine as stabilizer component is freed from its inhibitor content by distillation under a water-jet vacuum. The methacrylic acid collected as distillate is stabilized with vitamin E. Then the oligo-glycolic acid pre-condensate as initially obtained is esterified with the methacrylic acid in the solvent-free system in the presence of p-toluenesulfonic acid as catalyst and upon addition of a further amount of vitamin E. The progress of the esterification reaction is monitored. If required, small additional metered amounts of methacrylic acid will be subsequently added.

The resulting reaction product is eventually rendered acid-free by way of a dry neutralization with calcium hydroxide, and thereafter the solid neutralizing agent is removed therefrom over a pressurized filter.

The process steps as carried out are in detail described hereinbelow; the process is operated in a plurality of batches. The ageing behavior of the oligoglycolic acid pre-condensates stored in the absence of air is determined over the period of one year. It was be observed that the product properties remained constant.

In detail, the following is applicable:

2.1 Preparation of the glycolic acid/ethylene glycol 4:1 oligomer

A 25 l test reactor was charged with 16.72 kg of glycolic acid and 3.41 kg of ethylene glycol. The crystal pulp was melted in an inert atmosphere under a nitrogen stream and then further heated to a maximum temperature of 145° C. to 150° C. (bottoms temperature). After the reaction had started with distillation of water, it was continued for 11 hours until no more reaction water was formed (drop in the vapour temperature to 70° C. to 73° C. at a conversion of 70%). The aqueous solution obtained upon the distillation was analyzed for the quantity of distillate, the acid value (glycolic acid contents) and the water contents by the Karl Fischer method. In order to lead the reaction to completion, the mixture was carefully evacuated to 400 Torr, and the pressure was further reduced to 10 Torr within 2 hours and maintained at this level for 1 hour, in order to remove the residual water of reaction for accomplishing a quantitative conversion.

The excessive amount of condensate was collected for quantification in a cold trap (cooled with dry ice and ethanol). After the total period of reaction, the mixture was cooled to 100° C. and re-pressurized to atmospheric pressure with nitrogen, and the product was dispensed while still hot. The product was directly used for the preparation of oligo-glycolic acid bis-methacrylate without further purification.

2.2 Yield and mass balance

| Amount of distillate | | 4 222.8 g |
|---|---|---|
| Amount of glycolic acid = 263.58 g from the acid value (=46) | | −263.6 g |
| Determination of ethylene glycol by HPLC | | — |
| Amount of water (from the analysis by the Karl Fischer method) 91.6% in the distillate = =97.68% conversion. | | 3 868.1 g |

Analytical results of oligomers

| Designation | | Immediately after the preparation | 1 Month old | 1 Year old |
|---|---|---|---|---|
| Batch size | kg | 20 | 4.5 | 2 |
| Consistency | | pastous | pastous | pastous |
| Viscosity at room temperature (Epprecht Viscosimeter MK4) | mpa · s | 12,500 | 13,000 | 12,800 |
| Molecular weight | | | | |

-continued

Analytical results of oligomers

| Designation | | Immediately after the preparation | 1 Month old | 1 Year old |
|---|---|---|---|---|
| $M_n$* | | 438 | 455 | 454 |
| $M_W$ | | 515 | 533 | 530 |
| Free glycolic acid | % | 2.1/2.2 | 1.4 | 1.9 |
| Free ethylene glycol | % | 0.2 | 0.2 | 0.2 |
| Saponification value | | 765.4 | 754.4 | 754.0 |
| Behavior in water | | | | |
| pH after 2 minutes | | 3.8 | 3.8 | 3.8 |
| pH after 60 minutes | | 3.4 | 3.4 | 3.4 |
| Peroxide content | | negative | | |
| Analytical composition of the product Glycolic acid/ Ethylene glycol | | 3.975:1 | 3.972:1 | 3.972:1 |

*Determination of the molecular weight as GPC analysis. Since the calibration was effected with polyethylene glycol as standard, the difference between $M_n$ in theory and $M_n$ as found is due to the calibration method.

2.3 Oligo-glycolic acid bis-methacrylate

Commercially available methacrylic acid (company Röhm) is newly inhibited with vitamin E according to the following procedure:

In a vacuum distillation apparatus, 15 moles (= 1,291.35 g) of methacrylic acid (b.p. 163° C.) are admixed with 3.87 g (=3,000 ppm) of phenothiazine (as stabilizer); the methacrylic acid was distilled off under a strong stream of air in a water-jet vacuum. 100 ppm of vitamin E (Covitol F-1000-2, 67%, Henkel KGaA= 139 mg/l) are placed in the receiver, and the methacrylic acid is distilled with stirring. The distillation is stopped, once 932 g of the methacrylic acid have been collected after distillation.

2.4 Course of the reaction

A three-neck flask equipped with stirrer, Claisen head and condenser ("distillation bridge") is charged with 294 g of oligo-glycolic acid, 206.4 g methacrylic acid and 17.5 g of p-toluenesulfonic acid; the mixture is inhibited with 0.86 g of vitamin E (α-tocopherol). Throughout the reaction, air was passed through the mixture at a rate of at least 40 l/h.

The esterification is effected at a maximum temperature of 105° C. by removal of the water formed, until the quantity of water removed was more than 35.78 g (more than 97% conversion).

The distillation receiver was cooled with a dry ice/ethanol mixture throughout the reaction. At a maximum bottoms temperature of 105° C. and a pressure of 500 mbar the esterification time was between 12 and 14.5 hours at a total conversion of from 97 to 98.5%. The aqueous solution (as recovered from the receiver and cold trap) was sampled every 1.5 hours and was analyzed for the quantity of distillate, the acid value (methacrylic acid contents) and the water contents by the Karl Fischer method.

The water content and the amount of methacrylic acid as entrained in the distillation were calculated from the differences; after each determination, it was checked whether enough methacrylic acid was still available for the reaction. In most cases, additional 0.1 moles of methacrylic acid had to be replenished after about 7.5 or 8 hours.

Upon completion of the reaction (conversion in excess of 97%) the product was dispensed for purification.

2.5 Work-up of the reaction product

In the end of the reaction period, the product is not quite free from acid. Therefore, it was neutralized with $Ca(OH)_2$. Since in the determination of the acid value, due to the water required for the determination, the product underwent hydrolysis and a continuously increasing amount of acid was released by this reaction, it was not possible to determine the acid content by titration.

Therefore, the acid value had to be theoretically calculated.

The amount of Ca(OH)$_2$ calculated to be required for neutralization was introduced into the warm reaction product and allowed to react at 105° C. and 500 mbar with stirring and 40 l/h of air being passed through the mixture for 30 minutes.

The neutralized product (highly viscous at 100° C. to 105° C.) is filtered by means of a pressurized nutsch filter and a Loeffler filter (80NM012) at 100° C. to 105° C. under 3 bar.

Then, the product—while still hot—was once more filtered under otherwise the same conditions through a round filter (NNG 16, medium filtering speed).

EXAMPLE 3

A 25 liter glass reactor equipped with a Claisen head, condenser and receiver was charged with 15 kg of acrylic acid, inhibited with about 200 ppm of hydroquinone monomethylether and 30 g of α-tocopherol (Covitol F-1490 of the company Henkel KGaA). The acrylic acid was distilled at 50 mbar and 55° C., while 150 l/h of air were passed through the mixture. After the removal of about 3 liters of first runnings, the main fraction (7 kg) was distilled onto 3.6 g of α-tocopherol (Covitol F-1490), so that the distilled acrylic acid was inhibited with about 500 ppm of α-tocopherol.

+HL,3 Characteristic values:+HZ,1/32 ?

| Acid value: | 778 mg of KOH/g |
|---|---|
| Gardner color value: | <1 |
| Inhibitor content: | 490 ppm of α-tocopherol. |

EXAMPLE 4

A 2 liter glass reactor equipped with a Claisen head, condenser, receiver and stirrer was charged with weighed amounts of 800 g of an ethoxylated trimethylolpropane (OH value: 680 mg of KOH per 1 g of substance), 839.1 g of acrylic acid (inhibited with 490 ppm of α-tocopherol), 59.4 g of p-toluenesulfonic acid and 2.39 g of α-tocopherol (Convitol F-1490 of the company Henkel KGaA; total inhibition: 2,000 ppm of α-tocopherol, relative to the amount of product).

The esterification was carried out, while air (40 l/h) was passed through the mixture, and the excess of water and acrylic acid was removed. At a bottoms temperature of from 102° C. to 103° C., the esterification time was 8 hours, during which the vacuum profile was maintained as follows:

| From 0 to 60 min: | pressure reduced to 500 mbar; |
|---|---|
| from 60 to 300 min: | 500 mbar |
| from 300 to 420 min: | pressure reduced to 50 mbar; |
| from 420 to 480 min: | 50 mbar |

Characteristic values of the crude product:

| Acid value: | 20 mg of KOH/g |
|---|---|
| OH value: | 12 mg of KOH/g |
| Conversion | 96.9% |
| Gardner color value: | 11–12 |
| H$_2$O content: | 0.26%. |

The crude product was neutralized by the addition of 37.5 g of solid Ca(OH)$_2$ with stirring for 1 hour at 80° C. and 50 mbar, while air (40 l/h) was passed through the mixture and the water was removed.

| Acid value: | <1 mg of KOH/g |
|---|---|
| OH value: | 18 mg of KOH/g |
| Gardner color value: | 3–4 |
| H$_2$O content: | 0.10% |
| α-Tocopherol content: | 810 ppm. |

EXAMPLE 5

A 2 liter glass reactor equipped with a Claisen head, condenser, receiver and stirrer was charged with weighed amounts of 900 g of a propoxylated neopentylglycol (OH value: 460 mg of KOH per 1 g of substance), 638.1 g of acrylic acid (inhibited with 490 ppm of α-tocopherol), 55.8 g of p-toluenesulfonic acid and 2.29 g of α-tocopherol (Convitol F-1490 of the company Henkel KGaA; total inhibition: 2,000 ppm of α-tocopherol, relative to the amount of product).

The esterification was carried out, while air (40 l/h) was passed through the mixture, and the excess of water and acrylic acid was removed. At a bottoms temperature of from 102° C. to 103° C., the esterification time was 8 hours, during which the vacuum profile was maintained as follows:

| From 0 to 60 min: | pressure reduced to 500 mbar; |
|---|---|
| from 60 to 300 min: | 500 mbar |
| from 300 to 420 min: | pressure reduced to 50 mbar; |
| from 420 to 480 min: | 50 mbar |

| Acid value: | 25 mg of KOH/g |
|---|---|
| OH value: | 10 mg of KOH/g |
| Conversion | 96.6% |
| Gardner color value: | 8 |
| H$_2$O content: | 0.19%. |

The crude product was neutralized by the addition of 46.3 g of solid Ca(OH)$_2$ with stirring for 1 hour at 80° C. and 50 mbar, while air (40 l/h) was passed through the mixture and the water was removed.

| Acid value: | <1 mg of KOH/g |
|---|---|
| OH value: | 16 mg of KOH/g |
| Gardner color value: | 3 |
| H$_2$O content: | 0.11% |
| α-Tocopherol content: | 630 ppm. |

What is claimed is:
1. A surgical adhesive or cement free from physiologically unacceptable solvents for the adhesion-bonding of endogenous hard tissue or implants in a human or other animal body comprising

A) one or more polymerizable monofunctional or polyfunctional olefinically unsaturated compounds; and B) a polymerization inhibiting quantity of Vitamin E.

2. The surgical adhesive or cement of claim 1 wherein the polymerization inhibiting quantity of Vitamin E is from about 200 to about 10,000 ppm.

3. The surgical adhesive or cement of claim 2 wherein said quantity of Vitamin E is from about 300 to about 4,000 ppm.

4. The surgical adhesive or cement of claim 1 wherein said polymerizable monofunctional or polyfunctional olefinically unsaturated compounds are multifunctional or polyfunctional (meth)acrylates or combinations thereof.

5. The surgical adhesive or cement of claim 1 wherein the adhesive or cement is a two-component system wherein the first component is a monomer resin component containing the one or more polymerizable monofunctional or polyfunctional olefinically unsaturated compounds and the Vitamin E, and the second component is an initiator component.

6. The surgical adhesive or cement of claim 1 wherein the polymerizable monofunctional or polyfunctional olefinically unsaturated compounds are (meth)acrylic acid esters containing from 2 to 4 (meth)acrylate ester groups on a polyesteroligomer chain formed from at least one hydroxycarboxylic acid.

7. The surgical adhesive or cement of claim 6 wherein said polyester-oligomer chain is a hydroxyl-terminated oligomer chain produced by the reaction of hydroxycarboxylic acids, polyfunctional alcohols, and polyfunctional carboxylic acids.

8. The surgical adhesive or cement of claim 7 wherein two (meth)acrylate ester groups are present, one on each terminal hydroxy group at each end of the polyester oligomer chain.

9. The surgical adhesive or cement of claim 6 wherein the at least one hydroxycarboxylic acid is glycolic acid, lactic acid, hydroxybutyric acid, or combinations thereof.

10. The surgical adhesive or cement of claim 7 wherein said hydroxycarboxylic acid is lactic acid or glycolic acid and said polyfunctional alcohol is ethylene glycol or glycerol.

11. The surgical adhesive or cement of claim 6 wherein the (meth)acrylic acid esters have a number average molecular weight of from about 200 to about 600.

12. The surgical adhesive or cement of claim 11 wherein said number average molecular weight is from about 300 to about 500.

13. The surgical adhesive or cement of claim 6 wherein the (meth)acrylic acid esters have a viscosity of from about 500 to about 70,000 mPa's at room temperature.

14. The surgical adhesive or cement of claim 13 wherein said viscosity is from about 3,000 to about 50,000 mPa's.

15. A two-component surgical adhesive composition free from physiologically unacceptable solvents for the adhesion-bonding of endogenous hard tissue in a human or other animal body, wherein the adhesive when cured is resorbable by the body, consisting essentially of A) a monomer resin component comprising
  a) at least one (meth)acrylic acid ester containing from 2 to 4 (meth)acrylate ester groups on a polyesteroligomer chain formed from at least one hydroxycarboxylic acid, and
  b) a polymerization inhibiting quantity of Vitamin E; and B) an initiator component.

16. The surgical adhesive composition of claim 15 wherein said polyester-oligomer chain is a hydroxyl-terminated oligomer chain produced by the reaction of hydroxycarboxylic acids, polyfunctional alcohols, and polyfunctional carboxylic acids, and wherein two (meth)acrylate ester groups are present, one on each terminal hydroxy group at each end of the polyesteroligomer chain.

17. The surgical adhesive of claim 16 wherein said hydroxycarboxylic acid is lactic acid or glycolic acid and said polyfunctional alcohol is ethylene glycol or glycerol.

18. The surgical adhesive of claim 16 wherein the (meth)acrylic acid esters have a number average molecular weight of from about 300 to about 500.

19. The surgical adhesive of claim 15 wherein the methacrylic acid esters have a viscosity of from about 500 to about 70,000 mPa's at room temperature.

20. The surgical adhesive of claim 19 wherein said viscosity is from about 3,000 to about 50,000 mPa's.

* * * * *